United States Patent [19]

Hussain et al.

[11] 4,284,648

[45] Aug. 18, 1981

[54] NASAL ADMINISTRATION OF PROPRANOLOL

[75] Inventors: Anwar A. Hussain; Shinichiro Hirai; Rima Bawarshi, all of Lexington, Ky.

[73] Assignee: The University of Kentucky Research Foundation, Lexington, Ky.

[21] Appl. No.: 63,176

[22] Filed: Aug. 3, 1979

[51] Int. Cl.$^3$ .................... A61K 31/135; A61K 9/00
[52] U.S. Cl. .................................................. 424/330
[58] Field of Search ............................... 424/250, 330

[56] References Cited

PUBLICATIONS

Stern, Arzmit. Forsch, vol. 24, 1974, pp. 70–71.

Martindale, The Extra Pharm., Pharm. Press, London, 26th Ed., 1972, pp. 1582–1583.

*Primary Examiner*—Anna P. Fagelson
*Attorney, Agent, or Firm*—Burns, Doane, Swecker & Mathis

[57] ABSTRACT

The invention relates to a novel method of administering propranolol, a known β-andrenergic blocking agent widely used in the treatment of angina pectoris, arrhythmias, hypertension and other cardiac conditions, and migraine. The invention further relates to novel dosage forms of propranolol which are adapted for nasal administration and which include solutions, suspensions, gels and ointments.

7 Claims, 3 Drawing Figures

NASAL ADMINISTRATION OF PROPRANOLOL

BACKGROUND OF THE INVENTION

1. Field of the Invention

The present invention relates to a novel method of administering propranolol, a β-andrenergic-blocking agent, and to novel dosage forms containing propranolol adapted for nasal administration.

2. Description of the Prior Art

Propranolol, a β-andrenergic-blocking agent, is widely used therapeutically, chiefly in the management of hypertension and in the treatment of angina pectoris, arrhythmias and other cardiac conditions, and migraine. The drug is, however, inefficiently and variably absorbed from oral dosage forms. Thus, Shand et al, *Clin. Pharmacol. Therap.* 11, 112–120 (1970), report that a study in humans has shown that following oral administration of propranolol, peak plasma levels in five subjects given 80 mg oral doses varied seven fold, while levels for 10 mg intravenous doses in the same subjects varied only two fold. Furthermore, the bioavailability of propranolol in some subjects as calculated from the ratio of the area under the curve of an 80 mg oral dose and 10 mg I.V. dose was found to be as low as 16%. The variations in the blood levels as well as the low bioavailability for oral doses has been attributed by various researchers to the extensive metabolism of the drug in the gastrointestinal tract during the absorption process and/or to the effect of the first pass through the liver [Dollery et al, Ann, N.Y. Acad. Sci. 179, 109 (1971); Suzuki et al, *Chem, Pharm. Bull.* 20, 2731 (1972); and Garceau et al, *J. Pharm. Sci.* 67, 1360 (1978)].

SUMMARY OF THE INVENTION

In view of the foregoing, it is apparent that a serious need exists for the improved delivery of propranolol. Thus, it is an object of the present invention to provide novel dosage forms and a novel method of administering propranolol which will provide enhanced bioavailability and minimized variations in blood levels as compared to oral dosage forms, while at the same time providing relative ease of administration when compared to the intravenous route.

The foregoing object, resulting in bioavailability of propranolol comparable to that achieved by intravenous administration but without the disadvantages inherent in that route of administration, is achieved by nasal administration of propranolol. According to the invention, the propranolol is conveniently administered via a novel nasal dosage form, i.e., a solution, suspension, ointment or gel adapted for nasal administration.

DETAILED DESCRIPTION OF THE INVENTION

The word "propranolol" as used herein is intended to encompass any pharmaceutically acceptable form of propranolol, i.e., the free base or a pharmaceutically acceptable salt or ester thereof. Propranolol, or 1-(isopropylamino)-3-(1-naphthyloxy)-2-propanol, can be represented by the structural formula:

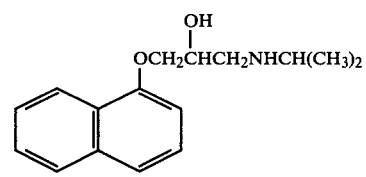

Details of the chemical synthesis of the free base, as well as a description of pharmaceutically acceptable esters and salts which can be derived therefrom, are set forth in Crowther et al U.S. Pat. No. 3,337,628, expressly incorporated by reference herein and relied upon.

According to the present invention, it has been surprisingly found that propranolol can be administered nasally with results considerably superior to those obtained with oral administration. The following study was undertaken to examine the bioavailability of propranolol from nasal solution in comparison with the bioavailability of the drug when administered orally and intravenously.

Sprague Dawley male rats, each weighing about 270 grams, were used in this study. For nasal administration, the rats were anesthetized using sodium pentobarbital (50 mg/kg) and the drug was administered to the nasal cavity by means of a micropipet at dosage levels of 1 mg/rat and 2 mg/rat in 0.1 ml of isotonic buffer solution (pH 7.2) according to the procedure described by Hirai et al, the 98th Annual Meeting of Pharmaceutical Society of Japan, Okayama, April 1978. For intravenous administration, the rats were anesthetized and a 1 mg dose of the drug in 0.2 ml isotonic buffer solution (pH 7.2) was injected into each rat through the femoral vein. After intravenous and nasal administration, blood from the femoral aorta was sampled periodically. For oral administration, the rats were not anesthetized and 1 mg/rat doses of the drug in 1 ml isotonic buffer solution (pH 7.2) were administered by means of a stomach tube. After oral administration, blood from the tail vein was sampled periodically. Blood levels of the drug were determined spectrophotofluorometrically by a minor modification of the method of Suzuki et al, *Chem. Pharm. Bull.* 20, 2731 (1972).

Figure 1:
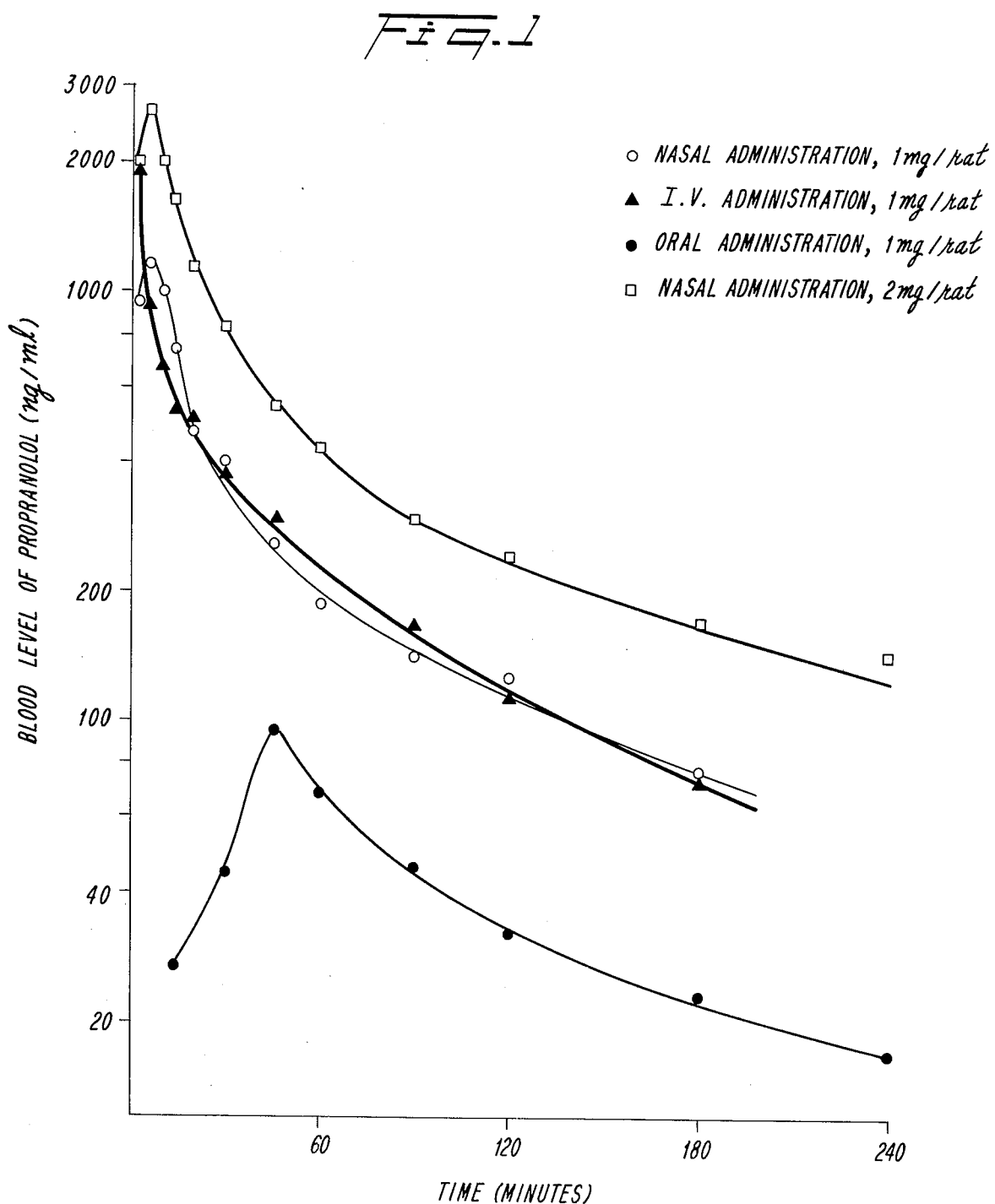
FIG. 1 is a semi-logarithmic plot of average blood levels of propranolol in rats obtained when the drug was administered via nasal, oral and intravenous routes.

FIG. 1 shows the mean blood levels of propranolol for the study described above. As seen from FIG. 1, the blood level of the drug after nasal administration of a 1 mg dose is identical to the blood level after intravenous administration of a 1 mg dose, whereas oral administration at the same dosage level results in considerably lower blood levels. The oral bioavailabilities calculated from the ratio of the area under the curve $$\frac{oral}{I.V.} \times 100 \text{ and } \frac{oral}{nasal} \times 100$$

within 4 hours after administration were found to be about 15%. Table I below shows the area under the curve (AUC) within 4 hours after intravenous, nasal and oral administration of propranolol (1 mg/rat) in rats.

TABLE I
AREA UNDER CURVE (AUC) WITHIN 4 HOURS AFTER INTRAVENOUS, NASAL AND ORAL ADMINISTRATION OF PROPRANOLOL (1 mg) IN RATS

| Route | AUC$^4$ (ng hr$^0$ml$^{-1}$) | Ratio | Percentage Absorbed Compared to I.V. Route |
|---|---|---|---|
| Intravenous | 807.2 ± 32.9* | — | |
| Nasal | 804.0 ± 56.4 | 0.996 | 99.6% |
| Oral | 144.5 ± 22.8 | 0.179 | 17.9% |

*mean ± SE

It can also be seen from FIG. 1 that the area under the blood level curve is directly proportional to the dose, when the drug is administered nasally. Further, it can be seen that propranolol is very rapidly absorbed from the nasal mucosa; thus, the peak plasma level is attained within 5 minutes of the instillation of the nose drops.

The advantages of nasal administration as compared to oral administration has also been demonstrated in tests in dogs. Details of the test procedure are set forth below.

Three beagle dogs weighing about 10 kg each were used for this crossover study. For nasal administration, the dogs were anesthetized with the intravenous injection of 30 mg/kg of sodium pentobarbital, and 0.2 ml of saline solution containing propranolol hydrochloride (20 mg/dog) was then administered to the nasal cavity via a micropipet. For intravenous administration, the dogs were anesthetized and a 20 mg/dog dose of the drug in 1.0 ml saline solution was injected through the foreleg vein. For oral administration, the dogs were not anesthetized and a 20 mg/dog dose of the drug in 50 ml of water was administered via a stomach tube. After nasal, intravenous and oral administration, blood was sampled from the foreleg vein periodically. Plasma levels of propranolol were determined spectrophotofluorometrically by a minor modification of the method of Shand et al, *Clin. Pharmacol. Therap.* 11, 112–120 (1970).

Figure 2:
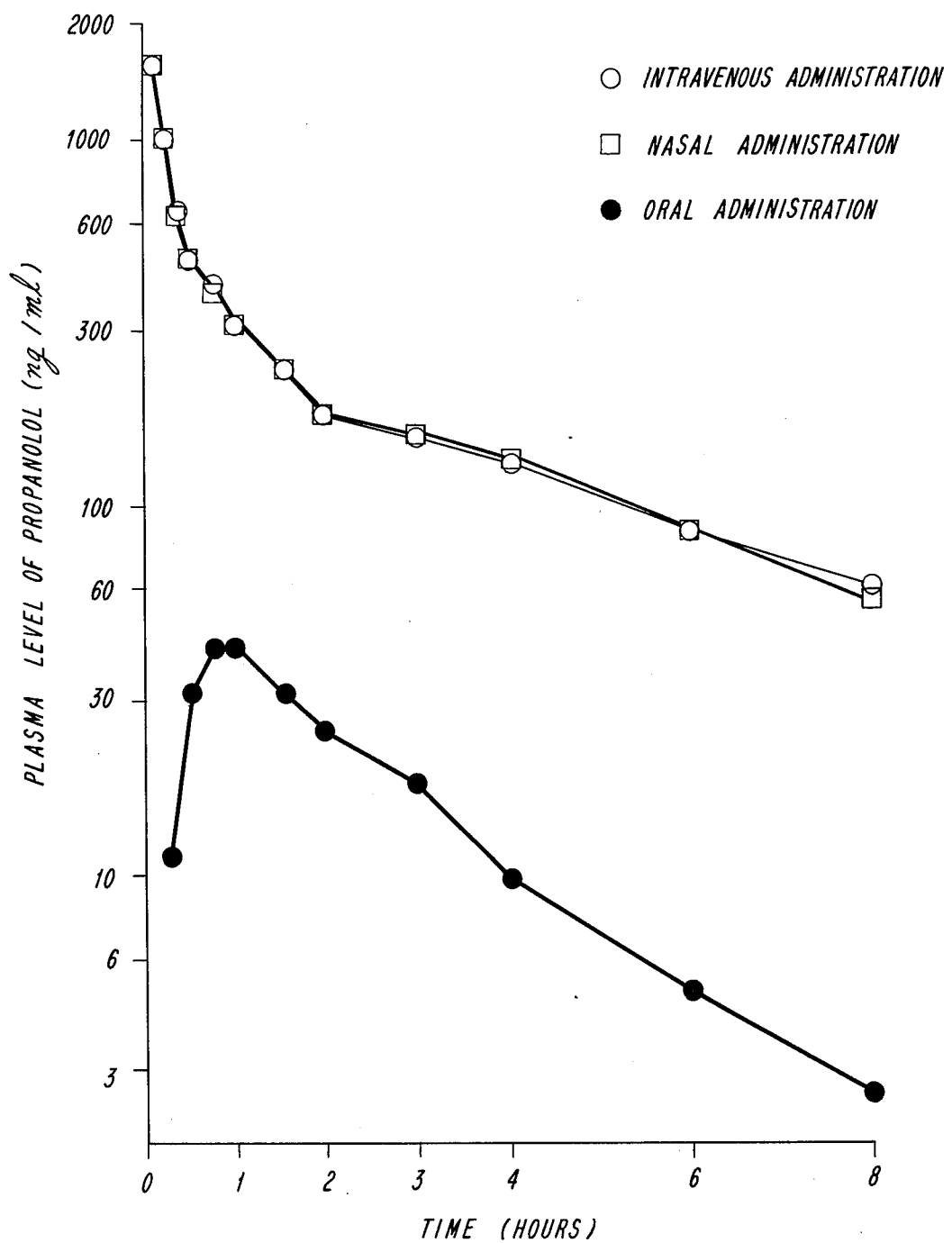
FIG. 2 is a semi-logarithmic plot of mean plasma levels of propranolol in dogs after administration of 20 mg doses via nasal, intravenous and oral administration.

FIG. 2 shows the mean plasma levels of propranolol for the study described immediately above. As can be seen from FIG. 2, the plasma levels of the drug after intravenous and nasal administration are virtually identical, whereas oral administration results in considerably lower plasma levels. Table II below summarizes the results obtained for each individual dog for the three routes of administration.

TABLE II
AREA UNDER PLASMA CURVE WITHIN 8 HOURS AFTER INTRAVENOUS, NASAL AND ORAL ADMINISTRATION OF PROPRANOLOL (20 mg) IN DOGS

| Dog | Intravenous (ng hr ml$^{-1}$) | Nasal (ng hr ml$^{-1}$) | Oral (ng hr ml$^{-1}$) | AUC (Nasal) / AUC (I.V.) | AUC (P.O.) / AUC (I.V.) |
|---|---|---|---|---|---|
| NJ06 | 1702.6 | 1648.0 | 151.8 | 0.967 | 0.089 |
| J096 | 1548.1 | 1538.9 | 93.8 | 0.994 | 0.059 |
| 1J96 | 1534.9 | 1556.3 | 117.9 | 1.013 | 0.076 |
| Mean | 1595.2 | 1581.0 | 120.8 | 0.991 | 0.074 |
| SE | 53.8 | 33.7 | 17.0 | 0.013 | 0.008 |

As can be seen from Table II supra, the bioavailability of propranolol from the oral route is only 7.4% of that of the intravenous route, whereas the bioavailability from the nasal route is 99.1% that of the intravenous route. These results and those from the study in rats detailed above indicate that propranolol is rapidly absorbed from the nasal mucosa into systemic blood without the first pass metabolism.

Propranolol can be conveniently administered nasally to warm-blooded animals by formulating it into a nasal dosage form comprising propranolol and a nontoxic pharmaceutically acceptable nasal carrier therefor. As indicated earlier, propranolol can be employed in the form of the free base or in the form of a pharmaceutically acceptable salt or ester thereof, e.g., propranolol hydrochloride or propranolol stearate. Suitable nontoxic pharmaceutically acceptable nasal carriers will be apparent to those skilled in the art of nasal pharmaceutical formulations. For those not skilled in the art, reference is made to the text entitled "REMINGTON'S PHARMACEUTICAL SCIENCES", 14th edition, 1970. Obviously, the choice of suitable carriers will depend on the exact nature of the particular nasal dosage form desired, e.g., whether propranolol is to be formulated into a nasal solution (for use as drops or as a spray), a nasal suspension, a nasal ointment or a nasal gel. Preferred nasal dosage forms are solutions and gels, which contain a major amount of water (preferably purified water) in addition to the active ingredient. Minor amounts of other ingredients such as pH adjusters (e.g., a base such as NaOH), buffering agents, preservatives, wetting agents and jelling agents (e.g., methylcellulose) may also be present.

Examples of the preparation of a typical nasal solution and of a sustained release nasal gel containing propranolol are set forth below. However, it is to be understood that these examples are given by way of illustration only and are not to be construed as limiting the invention either in spirit or in scope as many modifications both in materials and in methods will be apparent to those skilled in the art.

EXAMPLE 1

2 Grams of propranolol hydrochloride were dissolved in 80 ml of distilled water and the pH of the resultant solution was adjusted to 7.4 with dilute sodium hydroxide solution. A quantity of water sufficient to bring the total volume to 100 ml was then added. The solution was sterilized by being passed through a 0.2 micron Millipore filter.

EXAMPLE 2

80 Grams of water were heated to 80° C. and 3.0 grams of Methocel were added, with stirring. The resultant mixture was allowed to stand at room temperature for 3 hours. Then, 1.84 grams of propranolol stearate were suspended in 20 grams of water and the suspension was added to the gel and thoroughly mixed.

Figure 3:
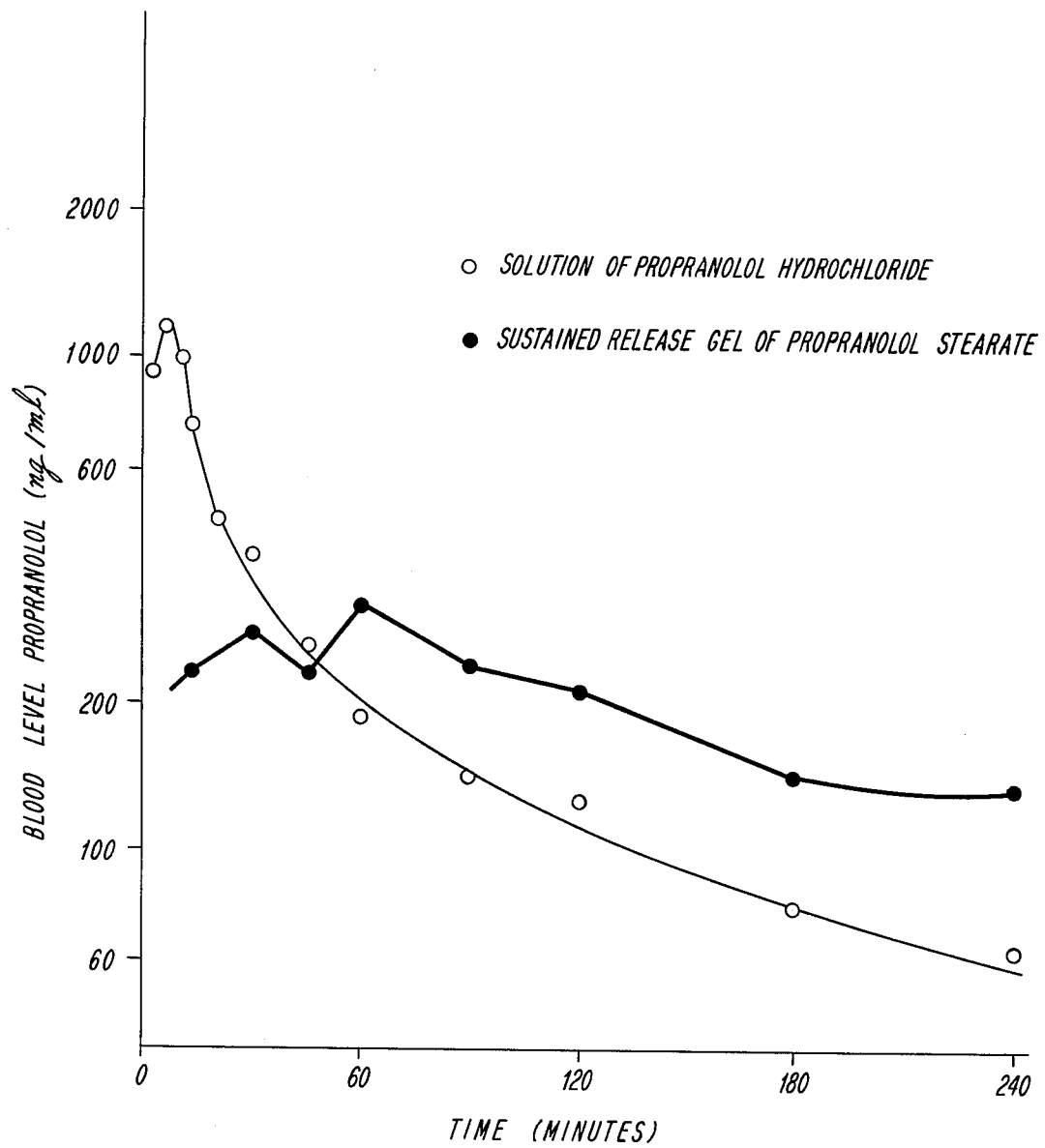
FIG 3 is a semi-logarithmic plot of mean blood levels of propranolol in rats after nasal administration of 1 mg doses via a nasal solution and via a sustained release nasal gel.

A sustained release gel prepared as described above was nasally administered to rats at the 1 mg/rat dosage level. FIG. 3 shows the mean blood levels of propranolol obtained as compared to those obtained for a 1 mg dose of nasal solution. The plot clearly shows that prolonged release of propranolol can be achieved via nasal administration.

EXAMPLE 3

A novel dosage form of an aqueous solution of propranolol in a pharmaceutical vehicle and suitable for use as nasal drops or nasal spray was prepared. The final composition, adjusted to pH 7.4, had the following composition:

| INGREDIENT | AMOUNT |
|---|---|
| propranolol hydrochloride | 500 mg |
| Tween 80 | 2 mg |
| methyl cellulose | 20 mg |
| water | 10 ml. |

Naturally, the therapeutic dosage range for nasal administration of propranolol acording to the present invention will vary with the size of the patient and the condition for which the drug is administered. A typical dose of propranolol would be 10 to 100 mg administered nasally three times daily. The quantity of nasal dosage form needed to deliver the desired dose will of course depend on the concentration of propranolol in the composition. The volume of solution or gel which would be needed to deliver the typical dose of active ingredient specified above would be 0.1 0.5 ml of 10% solution or gel.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method for eliciting a $\beta$-andrenergic blocking response in a warm-blooded animal in need of such therapy, comprising nasally administering to said animal a therapeutically effective amount of a compound having the formula:

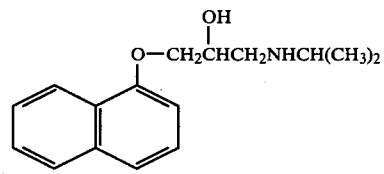

or nontoxic pharmaceutically acceptable derivative thereof.

2. The method as defined by claim 1, said compound being nasally administered together with a nontoxic pharmaceutically acceptable nasal carrier therefor.

3. The method as defined by claims 1 or 2, said animal being afflicted with angina pectoris.

4. The method as defined by claims 1 or 2, said animal being afflicted with arrhythmias.

5. The method as defined by claims 1 or 2, said animal being afflicted with hypertension.

6. The method as defined by claims 1 or 2, said animal being afflicted with migraine.

7. The method as defined by claim 2, said compound being administered from a form selected from the group consisting of nasal solution, nasal suspension, nasal ointment, nasal gel, and nasal sustained release gel.

* * * * *